United States Patent

Hellén et al.

Patent Number: 5,709,885
Date of Patent: Jan. 20, 1998

[54] PROCESS FOR THE PREPARATION OF DRUG PELLETS

[76] Inventors: Leena Hellén, Tuulensuunkatu 5 a, FIN-21100 Naantali; Isabelle Husson, Meriusva 5 as 43, FIN-02320 Espoo; Eeva Kristoffersson, Säynävätie 2 A, FIN-02170 Espoo; Jouko Yliruusi, Valkonauhantie 6 A, FIN-02700 Kauniainen, all of Finland

[21] Appl. No.: 411,804
[22] PCT Filed: Oct. 8, 1993
[86] PCT No.: PCT/FI93/00409
§ 371 Date: Jul. 31, 1995
§ 102(e) Date: Jul. 31, 1995
[87] PCT Pub. No.: WO94/08567
PCT Pub. Date: Apr. 28, 1994

[30] Foreign Application Priority Data

Oct. 9, 1992 [FI] Finland .................. 924590

[51] Int. Cl.$^6$ .................. A61K 9/14
[52] U.S. Cl. .................. 424/489; 424/470
[58] Field of Search .................. 424/493, 488, 424/489, 468, 490

[56] References Cited

U.S. PATENT DOCUMENTS

| | | | |
|---|---|---|---|
| 4,728,513 | 3/1988 | Ventouras | 424/461 |
| 4,882,169 | 11/1989 | Ventouras | 424/493 |
| 5,051,262 | 9/1991 | Panoz et al. | 424/468 |

FOREIGN PATENT DOCUMENTS

| | | |
|---|---|---|
| 162506 | 11/1991 | Denmark . |
| 0 486 959 A1 | 5/1992 | European Pat. Off. . |
| 59049840 | 3/1984 | Japan . |
| 2 234 899 | 2/1991 | United Kingdom . |
| 93/07859 | 4/1993 | WIPO . |

*Primary Examiner*—Thurman K. Page
*Assistant Examiner*—William E. Benston, Jr.
*Attorney, Agent, or Firm*—Marshall, O'Toole, Gerstein, Murray & Borun

[57] ABSTRACT

The object of the invention is a process for the preparation of drug pellets, which method comprises the stages according to which: a drug containing powder is granulated in a rotor type granulator, by exerting a centrifugal force on the powder in the rotor and bringing it, at the periphery of the rotor or adjacent thereto, in contact with a granulating liquid fed separately into the rotor and converted to a mist therein, to which granulating liquid an anti-adhesion agent in an amount of 0.001–5% of the weight of the granulating liquid has been added; the granulate is extruded; and the extrudate obtained is spheronized to pellets which are dried and optionally coated.

17 Claims, No Drawings

PROCESS FOR THE PREPARATION OF DRUG PELLETS

This application is a 371 of PCT/FI93/00409, filed Oct. 8, 1993.

The object of this invention is a process for the preparation of drug pellets, which method comprises the stages wherein a drug containing powder is granulated in a granulator which operates by the rotor principle, i.e. in a rotor type granulator, by exerting a centrifugal force on the powder and, at the periphery of the rotor or in its vicinity, bringing the powder in contact with a separately fed granulating liquid converted to a mist to make a granulate, extruding the granulate and spheronizing the extrudate obtained into pellets, which are dried and optionally coated.

Drug containing powders to be formulated into drug forms, such as pellets or tablets, seldom exhibit optimal formulation characteristics, such as flow, binding and solubility characteristics. Thus in order to provide optimal dosage forms the drug thus usually has to be combined with various adjuvants and additives which, on the one hand, impart to the dosage form suitable and desired characteristics and, on the other hand, facilitate the preparation of the dosage form.

In order to obtain a product of even quality, a granulate is first formed from the powder mixture containing adjuvants and additives, either by wet or by dry granulation, wherefrom subsequently pellets are formed and/or tablets are compressed.

Adjuvants generally in use in drug forms, such as pellets and tablets, are i.a. lactose, mannitol, microcrystalline cellulose, starch, sucrose, etc., the main purpose of which is to function as a filler or a diluent for the drug. Their amount as calculated from the final drug form can vary within wide limits, and can constitute even 99% or more of the weight of the whole formulation.

Binders are added to bind the powders and to prepare coherent drug formulations. Generally used binders are, for example, gelatin, various cellulose derivatives, polyvinyl-pyrrolidone, but also sucrose and starch may function as a binder. The binder is added either in dry form to the powder, or as a liquid. Binders are generally used in an amount of appr. 2–10% (w/w).

Glidants are added to the dry powders primarily in order to improve the pour and flow characteristics of the powders so that they may be fed at an even rate to the apparatus, thus allowing for the preparation of a product which is as homogenous as possible. The glidants are solid; typical glidants are colloidal silicon dioxide, magnesium stearate, starch and talcum. The amount to be added is naturally dependant on the powder used and also on the glidant, for example magnesium stearate is added to the powder in an amount of appr. 0.3–1%, whereas the amount of talcum to be added can be as high as 5%.

In the formulation, besides the above mentioned substances, also other adjuvants may be used, such as disintegrating agents and pH regulating agents. Surface active agents, such as polysorbates and sodium laurylsulfate have been proposed to be used for improving the wettability of the powder and the solubility of poorly soluble and hydrophobic drugs. It has been stated, however, that the addition of surface active agents to the treatment liquid should be avoided as such an addition makes the pellets so prepared brittle (Pharmaceutical Pelletization Technology, Drugs and the Pharmaceutical Sciences, vol. 37, Ed. I. Ghebre-Sellassie (Marcel Decker, 1989).

In the granulation, different kinds of mixing apparatuses have traditionally been used, e.g. high-shear or planetary mixers, which all operate on the batch principle, that is, they can be used for the manufacture of only one batch at a time. In order to obtain a good granulation result with these apparatuses, usually various adjuvants have to be added, for example binders or even organic solvents. Irrespective of carefully chosen substances and amounts it is not always possible to make, for example, a product which remains even as to its moisture content with a mixer of this type. This is naturally a big disadvantage especially in the preparation of drug forms. In addition, with regard to many drugs it would be of advantage if it were possible to eliminate the use of various additives in the drug formulations and thus raise the drug level itself.

According to the invention a method has now been developed which makes it possible to prepare drug pellets of very even quality with an apparatus, which includes a continuously operable granulator and an extruder and a spheronizer associated therewith.

The said granulator is of rotor type, wherein the powder and liquid, under the influence of the centrifugal force generated by a rapidly rotating rotor, are separately slung towards the periphery of the rotor, where or in the vicinity whereof the liquid dispersed into particulate form (mist) meets the powder and is mixed therewith to form an even granular mass. Such a mixer is in itself known and described for example in the EP-publication 254 791. More specifically, such an apparatus is formed by a rotor structure rotating in a housing and comprising, mounted on the same shaft, an upper disc provided, on its upper surface, with powder compartments restricted from above by the housing wall, into which compartments the powder is fed at the centre of the rotor, and a lower disc, which is spaced from the upper disc, into which space the liquid is fed. The discs rotate at e.g. 1000–5000 rpm, the peripheral speed being e.g. appr. 300–5000 m/min depending on the diameter of the rotor. The liquid is forced from the narrow slotlike space between the upper and lower rotors from its central feeding point towards the periphery of the rotor, where it exits as a mist through a narrow slit at the periphery of the upper rotor and where it meets the powder similarly forced by the centrifugal force towards the periphery, forming a very even granulate.

After granulation, the granulate obtained is fed to an extruder which preferably is of radial type, wherein the mass is extruded into ribbonlike bodies through a cylinder shaped perforated wall by means of rotor blades rotating within the cylinder about a central axis. Further, in the apparatus there are feeding blades rotating in an opposite direction with respect to the rotor blades, above these. Such an apparatus has been described e.g. in the EP-patent specification 163 619. Also other types of extruders can come into question.

After the extrusion stage, the extrudate obtained is spheronized in a spheronizer, for example in an apparatus of the type wherein the extrudate is rotated at great speed over a rotating friction plate. An apparatus suitable for the purpose is for example an apparatus of Nica or Caleva type.

According to a preferred embodiment, the different components of the assembly can be interconnected in order to provide for a continuous production line, and according to an especially advantageous embodiment, an assembly sold by the trade name Nica Systems, by Nica System Ab, Sweden, is used.

According to the invention it has been found that granulation, especially continuously performed granulation, as well as extrusion and spheronization, especially using a Nica Systems type of apparatus, can be substantially improved by adding to the granulating liquid a very small amount of a selective anti-adhesion agent, namely 0.001 to 5% by weight, but advantageously only 0.01–0.1% by weight, calculated from the weight of the granulating liquid.

As has been described above, glidants have been generally used in the formulation of drug forms, but such agents have been added directly as solid substances to the powder, primarily for improving its flow properties. According to the invention, however, the anti-adhesion agent is added to the granulating liquid, and the amount to be used according to the invention is also substantially smaller than the amounts used as described above.

The term "selective anti-adhesion agent" means in this context an agent which on the one hand improves the cohesiveness of the moist mass, and on the other hand prevents the adhesion of the moist mass to the various parts of the apparatuses used for the preparation. According to the invention it has been found that it also prevents the adhesion of the moist intermediate products, such as the moist extrudate or the moist pellets, to each other during the various stages of preparation, including drying.

According to the invention it has thus been observed that by adding a small amount of anti-adhesion agent to the granulating liquid, friction developed especially in the granulator but also in the extruder, and the resulting heating and adherence of the granular mass to the surfaces, can be eliminated to a substantial degree. This allows for operating the process in a continuous manner, with no process disturbances of any kind. In connection with the development of the invention, it has also been observed that without the said addition of anti-adhesion agent, the apparatus is often clogged or other disturbances occur. Overheating may also lead to problems with heat-sensitive drugs.

In the extrusion stage, in addition to the benefits mentioned above, the use of anti-adhesion agent also prevents the formation of a so called shark-skin extrudate, the further processing of which according to literature is not feasible as it leads to a wide size distribution range in the pellets. The anti-adhesion agent as used according to the invention provides an extrudate with good theological and good surface properties, which properties remain acceptable also during a continuous process.

The addition of selective anti-adhesion agent also facilitates the spheronization, while the friction plates, which provide for the spheronizing effect, remain clean and are not filled with drug mass, as is the case without the said agent. This applies also to a continuously operated process. Also the extrudate is spheronized more easily into pellets.

The use of anti-adhesion agent in accordance with the invention thus decisively improves the running of the process and makes it possible to operate the same in a continuous manner by assisting in the apparatus remaining clean, which naturally is a substantial advantage. It also improves the quality and evenness of the end product, i.a. provides rounder pellets. Thus the disadvantages of the earlier systems relating e.g. to variations in the particle size, may be eliminated, and product losses deriving therefrom, may be reduced.

By using the process according to the invention, the use of binder may in many cases be abandoned even completely, and pellets of even quality and with a high concentration of drug (even up to 95% drug) can be produced from merely a powdered drug and a filler, such a microcrystalline cellulose. The amount of filler can vary but usually it is at the most 30%, suitably appr. 5–20% by weight of the final formulation. There is no need to add further adjuvants and additives, but such may of course be added, e.g. buffers.

The selective anti-adhesion agent according to the invention does not belong to any specific pharmaceutical group of agents, such as for example lubricants or glidants, but according to the invention suitable anti-adhesion agents are preferably selected from the group formed by polyols, surface active agents, such as emulsifying and solubilizing agents and stabilizers, or silicone derivatives. Polyols are, for example, glycerol, propylene glycol, polyethylene glycol, e.g. PEGs 200–600 (Shell Chemicals Ltd); surface active agents, e.g. emulsifying and solubilizing agents and stabilizers are e.g. lecithin, poloxamer (e.g. Pluronic F-68, BASF Ltd), sodium lauryl sulfate (e.g. Tensopol, Tensla Ltd), polysorbates (e.g. Tween, Atlas Chemical In. Ltd), such as polysorbate 80, sorbitan esters (e.g. Span, Croda Chemicals Ltd), macrogols, dioctyl sodium sulfosuccinate (e.g. Docusate sodium, Manchem ltd), sodium laurylsulfonate; and silicone derivatives are e.g. silicone emulsions (e.g. Dow Corning 365 Medical Grade Emulsion, Dow Chemical Co.).

As the granulating liquid to which the anti-adhesion agent is added suitably for example water or a lower alcohol, e.g. ethanol, or their mixtures may be used. The amount of granulating liquid needed for granulation naturally depends on the powder to be granulated, the amount to be used being such which gives the desired rheological characteristics, and can be easily determined by a person skilled in the art. A suitable amount is usually in the area of 20–100% by weight calculated from the dry powder mixture, although smaller and larger amounts may be used. The amount of anti-adhesion agent remaining in the final formulation thus also depends on the amount of granulating liquid fed, a suitable final concentration varying between appr. 0.0002–5, suitably however appr. 0.002–0.1% by weight of the final product.

The following examples illustrate the invention without limiting the same in any way.

EXAMPLE 1

Pellets were prepared from powder mixtures containing always 80% by weight of the following drugs: diltiazem HCl, anhydrous theophylline, ibuprofen and paracetamol, as well as 20% by weight of microcrystalline cellulose (Emcocel 90 M, Edward Mendell Co., USA). As the granulating liquid, distilled water was used which contained 0–0.1% by weight (calculated from the water) of anti-adhesion agent. The anti-adhesion agent was polysorbate for the drugs in question. In the case of theophylline, also other agents were tested. The feeding rate for the water was adjusted so that its amount was 65% by weight of the fed powder mixture.

The drug and the microcrystalline cellulose powder were first mixed for 5 minutes in a high-shear-mixer (Fielder PMA 25, GB). The dry mass was granulated in a Nicamixer/granulator (Nica M6L, Sweden). The moist mass thus obtained was thereafter extruded in a Nica-extruder (Nica E140, Sweden) and finally spheronized in a Nica-spheronizor (Nica S320, Sweden). The granules were dried either at room temperature or in a vented oven.

In the following table the compositions of the final drug forms are given.

| Drug | Emcocel 90 | Polysorbate |
|---|---|---|
| Diltiazem.HCl | 79.98% | 19.99% | 0.03% |
| Ibuprofen | 79.97% | 19.99% | 0.04% |
| Paracetamol | 79.95% | 19.99% | 0.06% |
| Theophylline.anh. | 79.95% | 19.99% | 0.06% |

All the drug mixtures performed faultlessly in the process. From all the drugs, a pellet product was obtained which was of exceedingly even quality as to size distribution and composition, which product can be coated and/or used as such either as a capsule filling or compressed to tablets. The result was good even though the drugs used varied from very water soluble (diltiazem) to insoluble (ibuprofen).

As regards anhydrous theophylline, it was not possible to prepare pellets which contained more than 50% drug when using plain water as granulating liquid. The wet mass had in fact very bad self-lubricating properties and thus adhered to the apparatus giving rise to overheating in the mixing and extrusion stage. In order to eliminate this problem, small amounts of various anti-adhesion agents were added to the theophylline, i.e. those mentioned in the following table. 0.1% by weight of anti-adhesion agent was used calculated from the distilled water, except for dioctyl sodium sulfosuccinate (DOSS) where the amount added was 0.01% by weight.

| Composition (%) | I | II | III | IV | V |
|---|---|---|---|---|---|
| Theophylline | 79.95 | 79.95 | 79.95 | 79.95 | 79.95 |
| Emcocel 90M | 19.99 | 19.99 | 19.99 | 19.99 | 19.99 |
| Polysorbate 80 | 0.06 | | | | |
| Glycerol | | 0.06 | | | |
| PEG 300 | | | | 0.06 | |
| Silicone emulsion (silicone) | | | 0.06 | | |
| DOSS | | | | | 0.01 |

According to the invention it was possible to prepare also from theophylline pellets of even quality using different anti-adhesion agents.

We claim:

1. A process for preparation of drug pellets, comprising the steps of:
   granulating a drug-containing powder in a rotor-type granulator;
   contacting said drug-containing powder with a granulating liquid to produce a granulate, said granulating liquid comprising an anti-adhesion agent in an amount from about 0.001% to about 5.0% by weight of the granulating liquid;
   extruding said granulate;
   spheronizing said extruded granulate into pellets; and,
   drying said pellets.

2. The process according to claim 1, further comprising the step of converting said granulating liquid to a mist immediately prior to said contacting step.

3. The process according to claim 1, further comprising the step of coating said pellets subsequent to said drying step.

4. The process according to claim 1, wherein said anti-adhesion agent is present in said granulating liquid in an amount from about 0.01% to about 0.1% by weight.

5. The process according to claim 1, wherein said anti-adhesion agent is selected from the group consisting of polyols, surface-active agents, and silicone derivatives.

6. The process according to claim 5, wherein said anti-adhesion agent is a polyol selected from the group consisting of glycerol and polyethylene glycol.

7. The process according to claim 5, wherein said anti-adhesion agent is a surface-active agent selected from the group consisting of polysorbate and dioctyl sodium sulfosuccinate.

8. The process according to claim 1, wherein said granulating liquid is selected from the group consisting of water and lower alcohols.

9. The process according to claim 8, wherein said granulating liquid is buffered.

10. The process according to claim 1, wherein said granulating liquid is present in an amount from about 20% to about 100% by weight of the powder.

11. The process of claim 1, wherein said drug-containing powder comprises a drug selected from the group consisting of diltiazem, ibuprofen, theophylline, and paracetamol.

12. The process according to claim 1, wherein said drug-containing powder comprises a filler in an amount up to about 30% by weight of the powder.

13. The process according to claim 12, wherein said filler is present in an amount from about 5% to about 20% by weight of the powder.

14. The process according to claim 12, wherein said filler is microcrystalline cellulose.

15. The process according to claim 1, wherein said process is continuous.

16. A process for preparation of drug pellets, comprising the steps of:
   granulating a drug-containing powder in a rotor-type granulator, by exerting a centrifugal force on the powder in the rotor;
   contacting said drug-containing powder with a granulating liquid, at the periphery of the rotor or adjacent thereto, to produce a granulate, said granulating liquid comprising an anti-adhesion agent in an amount from about 0.001% to about 5.0% by weight of the granulating liquid;
   extruding said granulate;
   spheronizing said extruded granulate into pellets; and,
   drying said pellets.

17. The process according to claim 16, further comprising the step of coating said pellets subsequent to said drying step.

* * * * *